United States Patent [19]

Monico, Jr.

[11] Patent Number: 4,730,234

[45] Date of Patent: Mar. 8, 1988

[54] PIPE ASSEMBLY MODULE WITH INTERNAL ELECTRICAL CIRCUITRY

[76] Inventor: Michael A. Monico, Jr., 1300 Sonnet La., West Chester, Pa. 19380

[21] Appl. No.: 868,011

[22] Filed: May 29, 1986

[51] Int. Cl.[4] .................. F16L 39/00; H02B 1/04
[52] U.S. Cl. ............................. 361/384; 361/394; 361/420
[58] Field of Search ............ 339/16 R, 16 C, 16 RC; 174/47; 361/392, 393, 394, 395, 396, 383, 398, 384, 420

[56] References Cited

U.S. PATENT DOCUMENTS

| | | | |
|---|---|---|---|
| 1,798,356 | 3/1931 | Roth | 55/263 |
| 2,720,578 | 10/1955 | Caffiaux | 361/398 |
| 3,261,147 | 7/1966 | Allander | 55/222 |
| 3,733,782 | 5/1973 | Hatchel | 55/95 |
| 3,914,002 | 10/1975 | Berliner, et al. | 339/16 R |
| 3,989,330 | 11/1976 | Cullen | 339/16 R |
| 4,012,092 | 3/1977 | Godbey | 339/16 R |
| 4,016,943 | 4/1977 | Cullen | 339/96 |
| 4,121,193 | 10/1978 | Denison | 340/18 CM |
| 4,121,916 | 10/1978 | Fricke | 55/316 |
| 4,163,593 | 8/1979 | Kosik | 339/16 R |
| 4,256,474 | 3/1981 | Berger, et al. | 55/482 |
| 4,522,234 | 6/1985 | Kellner | 339/16 C |

*Primary Examiner*—G. P. Tolin
*Attorney, Agent, or Firm*—Steele, Gould & Fried

[57] ABSTRACT

The present invention relates to a means for extending an electrical circuit through a modular assembly comprising a plurality of threaded pipe modules which utilizes electrical contact strips. In particular, the circuit is extended through a system of interengagable outer pipe modules, adapted for use with one another, and for use with any of a plurality of inner pipe modules. Each of the modules is preferably a length of pipe having at least on its interior electrically insulating material and electrically conductive strips in a fixed spatial relationship. A precisely threaded coupling is formed on at least one end of the pipe having a single starting point for engagement with another precisely threaded coupling on another outer module.

5 Claims, 7 Drawing Figures

PIPE ASSEMBLY MODULE WITH INTERNAL ELECTRICAL CIRCUITRY

BACKGROUND OF THE INVENTION

1. Field of the Invention

The present invention relates to a means for extending an electrical circuit through a modular assembly. More particularly, the invention relates to a threaded pipe assembly module of circular cross-section which is adapted for use with similar modules to provide a housing and electrical circuitry for functional electrically operative systems.

2. Prior Art

It is known to extend an electrical circuit through an assembly of pipe material. U.S. Pat. No. 3,989,330 discloses a means for extending an electrical circuit through a kelly cock assembly. This patent discloses an electrical circuit which is formed by a hard wire conductor placed to one side of the kelly cock which terminates in contacts that are centered in the ends of the kelly cock body.

U.S. Pat. No. 4,016,943 also relates to a means for extending a circuit to a kelly. The system disclosed comprises a hard wire conductor disposed in the center of the bore of the kelly and exposed to drilling mud. The connector at the ends of the conductor are positioned in the ends of the kelly and serve to connect the conductor to the other equipment.

U.S. Pat. No. 4,121,193 relates to a hard wire telemetering system in which a circuit is extended through a saver sub utilizing contact rings disposed in sealing shoulders at each end of the saver sub. A circuit extends through a bore of the saver sub, and is anchored and sealed in a part at each end of the sub. An electrical conductor is placed in the conduit and joined to contact rings in the shoulders of the sub.

SUMMARY OF THE INVENTION

The present invention relates to a means for extending an electrical circuit through a modular assembly comprising a plurality of threaded pipe modules which utilizes electrical contact strips. In particular, the circuit is extended through a system of interengagable outer pipe modules, adapted for use with one another, and for use with any of a plurality of inner pipe modules. Each of the modules is preferably a length of pipe having at least on its interior electrically insulating material. At least one, and preferably at least two, electrically conductive strips are embedded in the insulating inner surface of the pipe, running the entire length thereof and forming electrical contact strips therein. A precisely threaded coupling is formed on at least one end of the pipe having a single starting point for engagement with another precisely threaded coupling on another outer module. The electrically conductive strips are placed so as to be in fixed spatial relationship to one another and to the fixed starting point for forming independent conductive paths in the module. As a result of the precise threading the conductive strips of coupled modules are automatically aligned respectively with one another. The inner modules are advantageously adapted to fit and slide snugly within any number of interengaged outer modules, and may contain outwardly facing electrical contacts adapted for respective connection along the length of the conductive strips. The respective contacts of the inner modules are in electrical contact with one another through the conductive paths irrespective of the specific and relative portions of the inner modules within any number of interengaged outer modules.

The system provides for the use of functional units which do not require electrical power that may be inserted into the interior of the modules. Also, electrically operative functional units or non-functional units are provided with the same precisely threaded couplings and the contact strips so as to have a continuous circuit.

The above construction provides a means by which conductive strips, including foils, rods and embedded electrically conductive materials which are in the module units, can extend the electrical circuit through the interior of the units. The module units may either be large size or of micro-size.

The system of the present invention can be utilized in the manufacture of heat exchangers, power transmitting devices, radio and audio components, medical apparatus and devices, flash lights and the like. The units are advantageously utilized where insulation against fluids is required.

It is therefore an object of the present invention to provide a means for extending an electrical current through a modular assembly which is either large size or micro-size.

It is a further object of the invention to provide an electrical circuit for use with functional electrically operative systems in a modular unit which permits quick and accurate alignment of the circuit.

It is yet still a further object of the invention to provide a fluid tight connection for a modular unit which is free of hard wire circuitry.

It is another object of the invention to provide a modular assembly having interconnected electrical circuits which can be quickly assembled or disassembled, that is rugged in construction, simple in design and during assembly can precisely align the circuits.

Other objects and a fuller understanding of the invention will be had by referring to the following description and claims of a preferred embodiment, taken in conjunction with the accompanying drawings, wherein like reference characters refer to similar parts throughout the several views.

DESCRIPTION OF THE PREFERRED EMBODIMENT OF THE INVENTION

Figure 1:
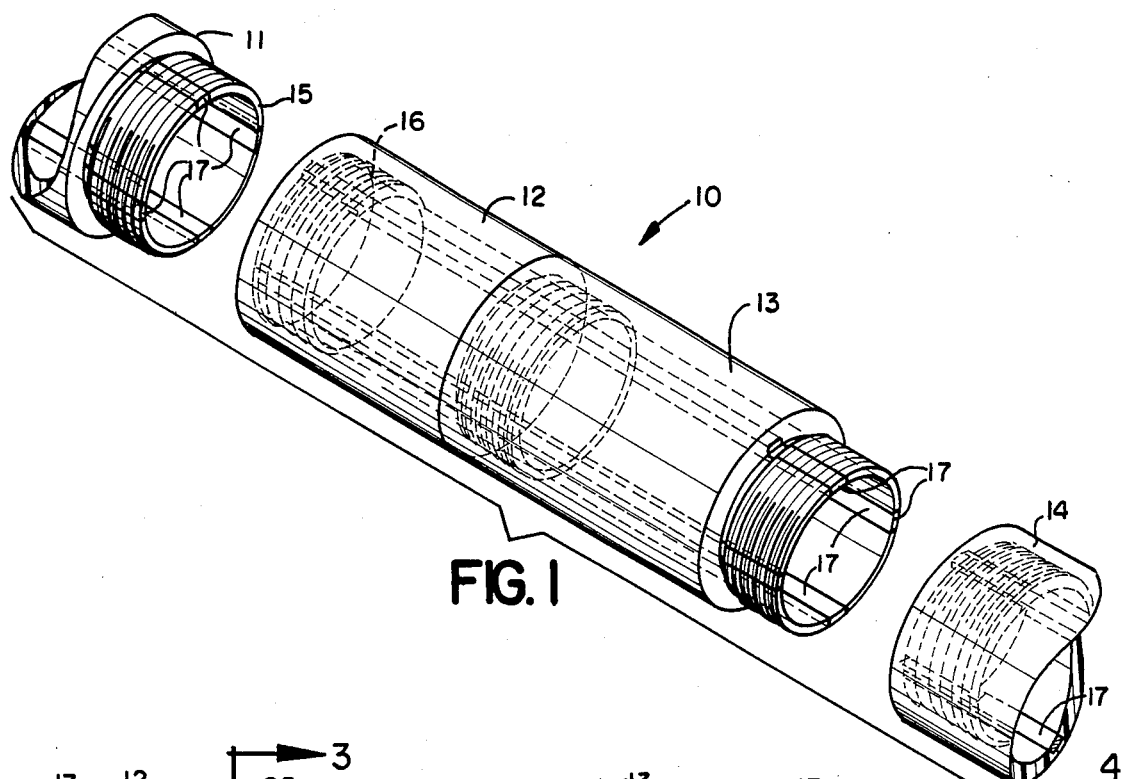
FIG. 1 is a side elevation, partly in section disclosing a modular unit of the invention.

Although specific terms are used in the following description for the sake of clarity, these terms are intended to refer only to the particular structure of the invention selected for illustration in the drawings, and are not intended to define or limit the scope of the invention.

Referring now to the drawings, as seen in FIG. 1, an assembly 10 consisting of pipes of modules 11, 12, 13 and 14 having a threaded male coupling 15 and a female coupling 16. Along the length of each of the modules 11, 12, 13 and 14 there is provided strips 17 of electrically conductive material. As shown, when the modules are threaded, the conductive strips of each of the modules are precisely aligned so as to provide an effective electrical contact between the modules.

The threaded couplings 15, 16 have a single starting point for engagement with another precisely threaded coupling of other modules. There is further provided a predetermined spatial relationship between the single starting point and the conductive strips 17 whereby the conductive strips 17 of the coupled modules are automatically aligned with one another in substantial surface across the interengaged couplings.

The modules 11, 12, 13 and 14 of the assembly 10 have an internal circular cross-section and are adapted for use with other similar modules or function units and/or power sources.

The module units may be of electrically insulating material such as a polyolefin resin, for example, polyethylene, polypropylene, etc., polyvinyl acetate, nylon, Teflon, or any other moldable thermoplastic or thermosetting resin. The modules may also be formed of a metallic outer portion and an inner portion of electrically insulative material.

The electrically conductive material may be foil, rods, electrically conductive particles or the like which may either be formed in or placed on the insulative surface. The conductive strips when embedded in the insulative surface are sufficiently thick to present an inner contact surface on the female coupling and on the outer contact surface of the male coupling. Where there are two or more electrically conductive strips, the strips are usually in a fixed spatial relationship to one another and to the fixed starting point so as to provide alignment of the strips respectively with one another in substantial surface contact across the interengaged threaded couplings while maintaining the respective integrity and relative independence of the conductive paths. Advantageously, the conductive paths are circumferentially equiangularly spaced from one another. When required, there may be at least one electrical contact disposed on the other surface of the assembly which is electrically connected to at least one of the electrically conductive strips. In accordance with such an arrangement it is possible to provide switch means or other functional units for the assembly.

It is also advantageous to utilize functional units which can be inserted into the interior of the modules, for example, an odorizing or deodorizing unit wherein no electrical contact is needed. In such cases screen units can be utilized in order to retain the functional unit within a module.

Figure 2:
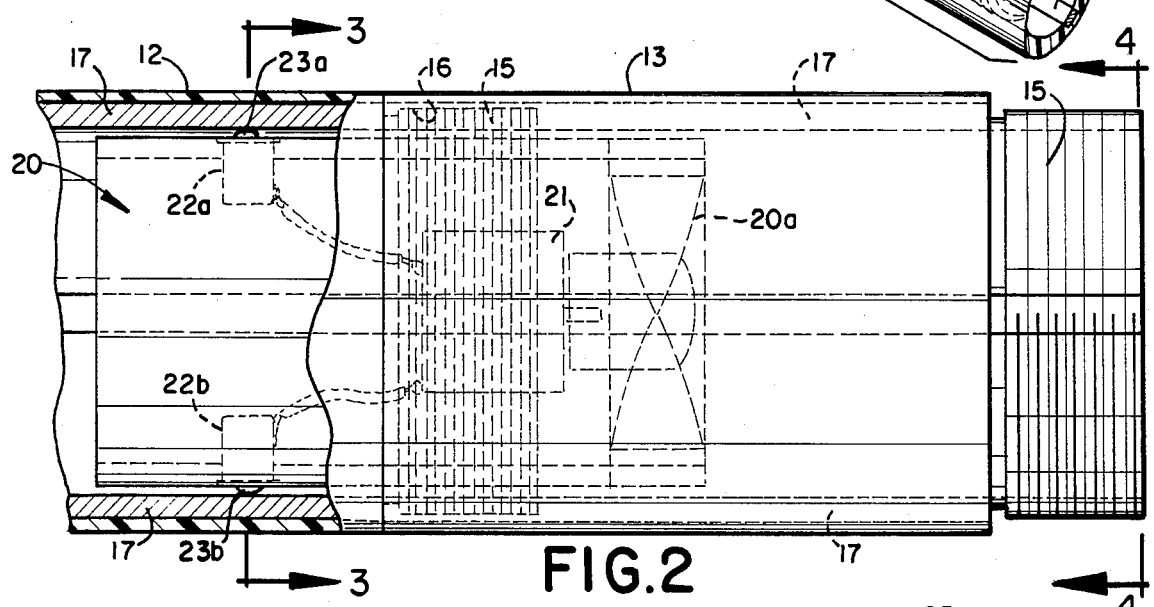
FIG. 2 is an elevational view showing a section of the modular unit of FIG. 1.
Figure 3:
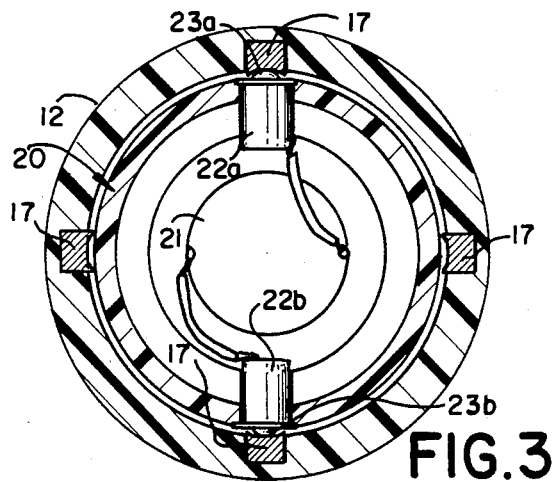
FIG. 3 is a cross section on line 2—2 of FIG. 2.
Figure 4:
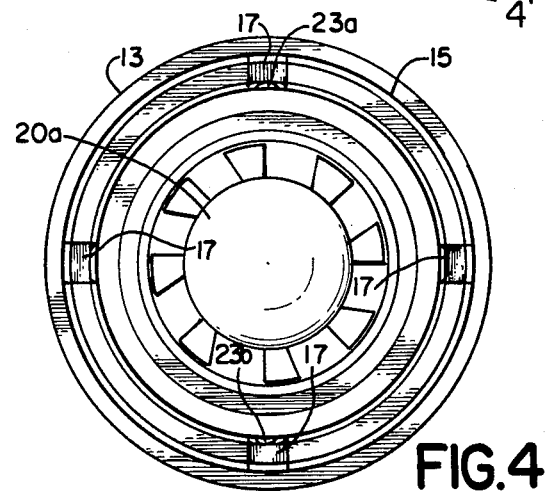
FIG. 4 is a cross section on line 3—3 of FIG. 2.

In FIG. 2 there is shown the modules 12 and 13 with a functional unit 20 which houses a fan 20a. The fan 20 has a motor means 21 and electrical contactors 22a, 22b. Optionally, as shown in FIGS. 3 and 4, the contact strip 17 may be slightly recessed so that the contactors 22a, 22b are securely held in constant contact with the strips 17. The fan 20a is made operational by the attachment of module unit 11 which contains a battery (not shown). A recess is not necessary where the functional units are formed in module units having the contact strips 17 and the precisely threaded couplings 15, 16.

Figure 5A:
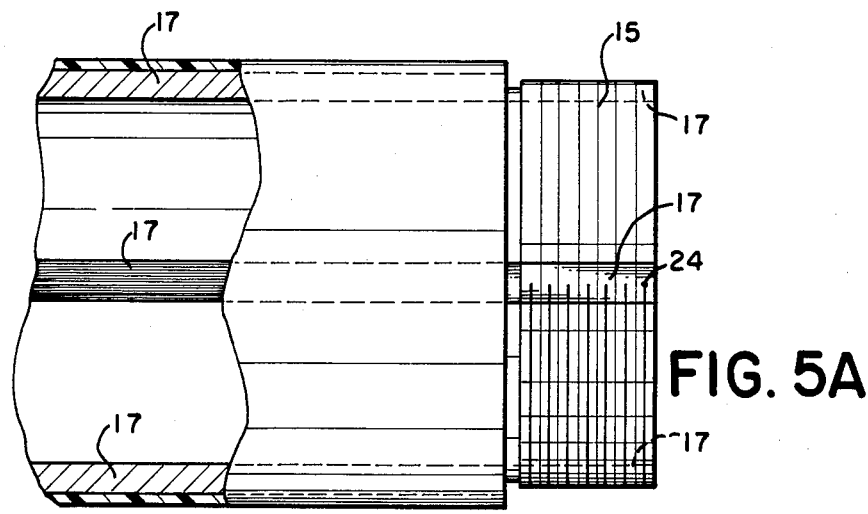
FIGS. 5A and 5B are side elevations in section of couplings for the modules of the assembly.
Figure 5B:
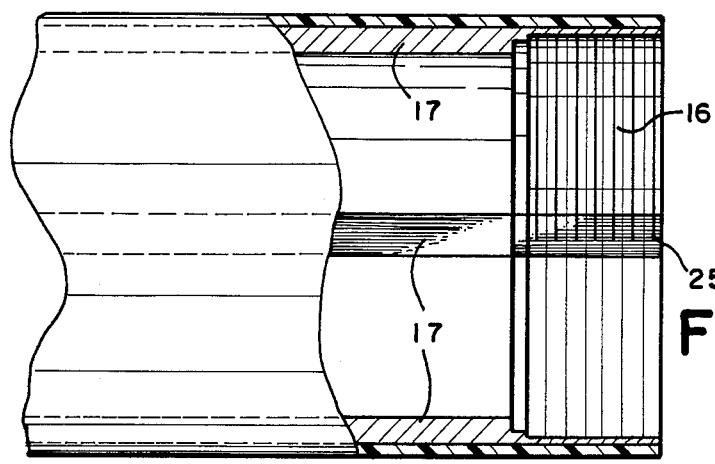

In FIGS. 5A and 5B the precisely threaded couplings 15, 16 are shown with their common starting points 24, 25. Advantageously, when the units are to be coupled, rotation begins with proper alignment of strips 17.

Although a male coupling 15 and a female coupling 16 are shown, the invention also contemplates the joining of two modules either at their male couplings or female couplings through the use of functional units which for example, are provided with outside threads so as to be threaded between two modules through the male coupling 15.

Figure 6:
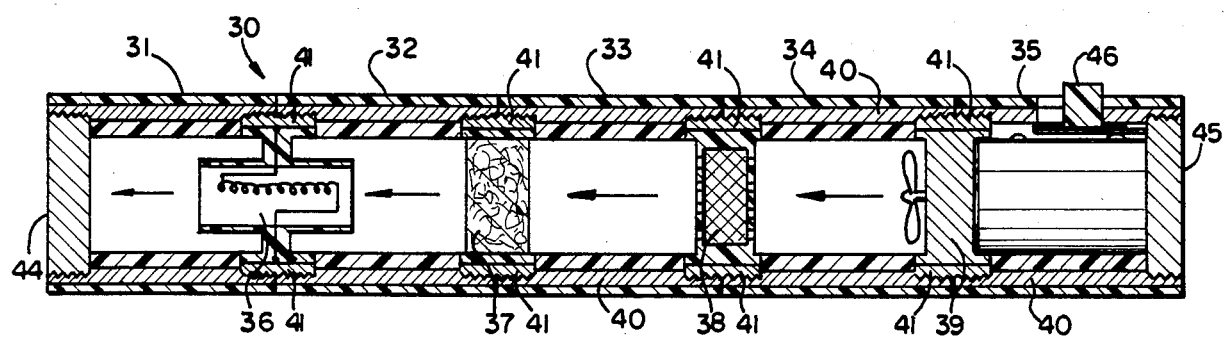
FIG. 6 is a side elevation in section of a modular unit provided with functional units.

In FIG. 6 there is shown an assembly 30 composed of a plurality of module units 31, 32, 33, 34 and 35 having electrical contact strips 40 which are interconnected with threaded engaging functional units 36, 37, 38 and 39. The functional units each have a electrically conductive material 41 running the entire length and forming electrical contact with the contact strips 40 through the entire assembly. The module units 31, 32, 33, 34 and 35 are all precisely threaded so as to couple together the functional unit 36, 37, 38, 39 which are composed only of male couplings. All of the couplings begin from a similar starting point and having the threads ending so as to automatically align the conductive strips both at the beginning of the threading and at the end.

The assembly 30 may be composed, for example, of functional units such as a fan and motor means 39 which blows air through a deodorizing unit 38 which may contain an odorant. The odorized air then passes through a filter unit 37 and then through a heater unit 36. The assembly 30 may be enclosed at each end by end caps 44 and 45.

In place of end cap 44 there may be utilized a filter unit 37. The filter unit is also provided with an electrically conductive strip so that the assembly 30 can be expanded with other functional units if desired.

As seen on module 35, there may be provided a unit in which the conductive path is broken and leads to the surface of the module for placement of a sliding switch 46. The sliding switch 46 permits the completion or breaking of the conductive path which can also be broken by merely twisting or rotating one of the units out of alignment.

To form a water-tight coupling there may be employed any of the conventional pipe joint compounds, for example, a Teflon thread.

Although the invention has been described with a certain degree of particularly, it is understood that the present disclosure has been made only by way of example and that numerous changes in the details of construction and the combination and arrangement of parts may be resorted to without departing from the spirit and scope of the invention.

What is claimed is:

1. A system of interengageable pipe modules, adapted for use with one another and with a functional unit, comprising:

at least two lengths of pipe of electrically insulating material and having an internal circular cross-section, each forming an outer module;

at least two electrically conductive strips on the inner surface of each of the at least two pipes and a functional electrically operative unit making contact therewith, running the entire lengths thereof;

a precisely threaded coupling formed on at least one end of each of the at least two pipes and a functional electrically operative unit, one of the at least two pipes and a functional electrically operative unit having a male coupling and the other having a female coupling, each of the couplings having a single starting point and being an engagement with another outer module and each of the at least two conductive strips in each of the at least two modules and a functional electrically operative unit spatial relationship to one another and to the single starting point, the at least two conductive strips of coupled outer modules and a functional operative unit being automatically aligned respectively with one another and in surface contact across the interengaged threaded couplings;

each of the at least two conductive strips being sufficiently thick and forming an inner contact surface on female couplings and an outer contact surface on male couplings, and a contact surface on said functional electrically operative unit;

at least one inner module adapted to fit and slide snugly within any number of interengaged outer modules, the at least one inner module having interengaged outer modules therearound, the at least two conductive strips, respective contacts of the at least one inner module being in electrical contact with the at least two conductive strips irrespective of the specific and relative positions of the inner module within any number of interengaged outer modules, and wherein the at least one inner module comprises electrical battery means and has axial fluid flow passages therethrough, another one of the inner modules comprises an electrically operative functional unit which is an electrically driven fan means, each of the electrically conductive strips forming a power bus between the electrical battery means and the electrically driven fan means, and yet another of the inner modules comprises air filtering means, whereby air may be driven through an assembly of interengaged outer modules, and filtered during through an assembly of interengaged outer modules, and filtered during passage therethrough, irrespective of the relative positions of the inner modules.

2. The system of claim 1, wherein three conductive strips are present and circumferentially equiangularly spaced from one another.

3. The system of claim 1, wherein at least one modules comprises an outer surface electrical contact for each conductive strip, providing electrical communication for each electrically conductive strip between the exterior and interior of a modular assembly.

4. The system of claim 1, further comprising one inner module within an outer module wherein said inner module is without outwardly facing electrical contacts.

5. The system of claim 1 including at least two inner modules which fit and slide snugly within outer modules, the at least two inner modules each having outwardly facing electrical contacts adapted for respective connection along the length of the at least two conductive strips, respective contacts of each of the at least two inner modules being in electrical contact with one another through the at least two conductive strips.

* * * * *